(12) United States Patent
Goldberg et al.

(10) Patent No.: US 10,327,945 B2
(45) Date of Patent: Jun. 25, 2019

(54) MAGNETIC EYE SHIELDS AND METHODS OF TREATMENT AND DIAGNOSIS USING THE SAME

(71) Applicant: EMMETROPE OPHTHALMICS LLC, Key Biscayne, FL (US)

(72) Inventors: Jeffrey L. Goldberg, Menlo Park, CA (US); Roger A. Goldberg, Lafayette, CA (US); Noelia J. Kunzevitzky, La Jolla, CA (US); Dillon Joseph Rak, San Diego, CA (US)

(73) Assignee: Emmetrope, Inc., Key Biscayne, FL (US)

( * ) Notice: Subject to any disclaimer, the term of this patent is extended or adjusted under 35 U.S.C. 154(b) by 749 days.

(21) Appl. No.: 14/706,701

(22) Filed: May 7, 2015

(65) Prior Publication Data

US 2015/0238357 A1    Aug. 27, 2015

Related U.S. Application Data

(63) Continuation-in-part of application No. PCT/US2013/068397, filed on Nov. 5, 2013.
(Continued)

(51) Int. Cl.
*A61F 9/00* (2006.01)
*A61K 41/00* (2006.01)
(Continued)

(52) U.S. Cl.
CPC ............ *A61F 9/0008* (2013.01); *A61K 41/00* (2013.01); *A61N 2/00* (2013.01); *A61N 2/06* (2013.01)

(58) Field of Classification Search
CPC ........................ A61N 2/00; A61N 2/06; A61F 9/0008; A61F 2210/009; A61F 2007/009;
(Continued)

(56) References Cited

U.S. PATENT DOCUMENTS 5,762,599 A * 6/1998 Sohn ..................... A61F 2/0018
417/420
6,131,208 A    10/2000 Banks
(Continued)

FOREIGN PATENT DOCUMENTS

CN    201304079 Y    9/2009
WO    2009000478 A1    12/2008

OTHER PUBLICATIONS

Mimura et al., Invest. Ophthalmol. Vis. Sci. 2005, 46(10):3637-44
T. Mimura et al., "Treatment of rabbit bullous keratopathy with precursors derived from cultured human corneal endothelium", Invest Ophthalmol Vis Sci 2005; 46: 3637-44 (Abstract).

*Primary Examiner* — Adam Marcetich (57) ABSTRACT

In certain aspects, the invention is directed to magnetic eye shields that comprise a magnet. When worn by a patient, the magnetic eye shields are configured to generate an intraocular magnetic field of sufficient magnitude and direction to move a magnetic therapeutic and/or diagnostic agent positioned inside the eye to target tissue within the eye. Other aspects of the invention pertain to kits which comprise such magnetic eye shields as well as one or more additional components, for example, one or more containers of a magnetic diagnostic and/or or therapeutic agent. Further aspects of the invention pertain to methods of treatment, which comprise intraocularly introducing a magnetic therapeutic and/or diagnostic agent into an eye of a patient and fitting a magnetic eye shield to the head of the patient, wherein the magnetic therapeutic and/or diagnostic agent may be introduced to the patient before or after fitting the magnetic eye shield to the head of the patient.

28 Claims, 5 Drawing Sheets

Related U.S. Application Data (60) Provisional application No. 61/723,475, filed on Nov. 7, 2012.

(51) Int. Cl.
  *A61N 2/00* (2006.01)
  *A61N 2/06* (2006.01)

(58) Field of Classification Search
  CPC .......... A61K 41/00; A61M 2037/0007; A61M 2205/0272; A61M 2205/057; A61M 1/3618
  See application file for complete search history.

(56) References Cited

U.S. PATENT DOCUMENTS

| | | | |
|---|---|---|---|
| 6,344,021 B1* | 2/2002 | Juster | A61N 2/06 600/15 |
| 6,406,419 B1 | 6/2002 | Farahmand | |
| 7,176,386 B1* | 2/2007 | Aidam | G21F 5/00 174/391 |
| 2002/0147424 A1* | 10/2002 | Ostrow | A61M 37/00 604/20 |
| 2002/0198433 A1* | 12/2002 | Roberts | A61N 2/008 600/9 |
| 2003/0056281 A1 | 3/2003 | Hasegawa | |
| 2003/0217754 A1* | 11/2003 | Thomas | A61N 1/16 128/856 |
| 2004/0012470 A1* | 1/2004 | Zimmerling | A61N 1/37 335/207 |
| 2004/0086572 A1* | 5/2004 | Dailey | A61K 9/0043 424/489 |
| 2004/0133099 A1* | 7/2004 | Dyer, Jr. | A61K 9/0046 600/420 |
| 2004/0171970 A1* | 9/2004 | Schleuniger | A61B 8/546 601/2 |
| 2005/0203333 A1* | 9/2005 | Dailey | A61F 2/147 600/37 |
| 2006/0083931 A1* | 4/2006 | Wadle | H05K 9/0075 428/432 |
| 2006/0228421 A1* | 10/2006 | Seeney | A61N 2/12 424/489 |
| 2006/0264690 A1* | 11/2006 | Ochi | A61K 41/00 600/9 |
| 2007/0010702 A1* | 1/2007 | Wang | A61F 2/82 600/8 |
| 2007/0073096 A1 | 3/2007 | Alvarado | |
| 2008/0002149 A1* | 1/2008 | Fritsch | G02C 7/04 351/159.02 |
| 2009/0030261 A1 | 1/2009 | Whitmore | |
| 2009/0093669 A1* | 4/2009 | Farone | A61K 31/137 600/15 |
| 2009/0156884 A1* | 6/2009 | Schneider | A61N 2/02 600/14 |
| 2010/0137779 A1* | 6/2010 | Seitz | A61N 1/30 604/20 |
| 2010/0212676 A1* | 8/2010 | Shapiro | A61M 37/0092 128/899 |
| 2010/0286468 A1* | 11/2010 | Mishelevich | A61N 2/006 600/12 |
| 2011/0003003 A1 | 1/2011 | Goldberg et al. | |
| 2011/0190569 A1* | 8/2011 | Simon | A61N 1/40 600/26 |
| 2011/0201869 A1* | 8/2011 | Edwards | A61M 37/00 600/15 |
| 2011/0272189 A1* | 11/2011 | Chen | H01F 27/36 174/377 |
| 2012/0226265 A1 | 9/2012 | Chiao | |
| 2013/0231520 A1* | 9/2013 | Cherian | A61F 2/14 600/12 |
| 2013/0261374 A1* | 10/2013 | Elder | A61N 2/008 600/15 |
| 2014/0056813 A1* | 2/2014 | Pottier | A61K 9/1271 424/9.1 |
| 2014/0243583 A1* | 8/2014 | Neroev | A61H 5/00 600/9 |
| 2015/0305929 A1* | 10/2015 | Goldberg | G02B 1/043 604/521 |
| 2016/0038590 A1* | 2/2016 | Li | A61K 31/277 514/44 A |

* cited by examiner

MAGNETIC EYE SHIELDS AND METHODS OF TREATMENT AND DIAGNOSIS USING THE SAME

STATEMENT OF RELATED APPLICATION

This application is a continuation-in-part of international application Serial No. PCT/US2013/068397 filed Nov. 5, 2013 and entitled "MAGNETIC EYE SHIELDS AND METHODS OF TREATMENT AND DIAGNOSIS USING THE SAME," which claims the benefit of U.S. Ser. No. 61/723,475, filed Nov. 7, 2012 and entitled: "MAGNETIC EYE SHIELDS AND METHODS OF TREATMENT AND DIAGNOSIS USING THE SAME," each of which is hereby incorporated by reference in its entirety.

FIELD OF THE INVENTION

The present invention is related to magnetic eye shields and to methods of treatment and diagnosis using magnetic eye shields.

BACKGROUND

Figure 1:
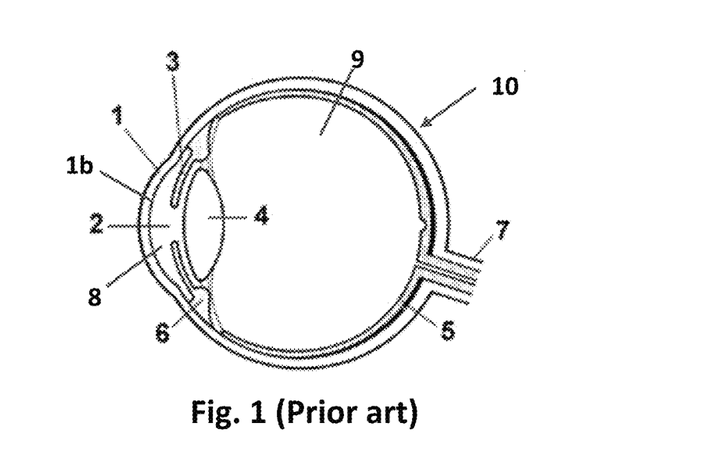
FIG. 1 is a schematic illustration of a human eye in accordance with the prior art.

A large number of diseases and disorders result from the dysfunction of a specific tissue or organ. A number of these diseases and disorders are currently treated by transplantation, e.g., heart transplantation for certain types of cardiac dysfunction, corneal transplantation for corneal endothelial cell dysfunction, stem cells for blood cancers, and so forth. However, transplantation procedures are invasive, have varying rates of success, and are not available for many types of injuries, diseases or disorders, in particular for a number of eye diseases, for example, including certain injuries or diseases of the cornea (e.g., endothelial dystrophies, stromal dystrophies, bullous keratopathy, etc.), certain injuries or diseases of retinal ganglion cells and the optic nerve (e.g., glaucoma, retinal artery or vein occlusions, ischemic optic neuropathies, other optic neuropathies, etc.), and certain diseases of retinal photoreceptors and retinal pigment epithelium (e.g., Leber's congenital amaurosis, retinitis pigmentosa, age-related macular degeneration, etc.) For ease of reference, various parts of the eye 10 are shown in FIG. 1, specifically, the cornea 1, pupil 2, iris 3, ciliary muscle 6, lens 4, retina 5, optic nerve 7 and anterior chamber 8 (which contains the aqueous humor), and vitreous cavity 9.

Although in many cases it would seem desirable to administer new "healthy" cells, for instance, by injection or infusion, simply introducing such cells into the eye generally does not work as they do not remain localized and adhere to or become incorporated into the target tissue of a patient. For example, healthy corneal endothelial cells are inefficiently incorporated into a patient's diseased or injured cornea when injected into the anterior chamber of the eye, with the majority of cells simply falling by gravity away from the cornea, rather than properly attaching to the cornea (see, e.g., Mimura et al., *Invest. Ophthalmol. Vis. Sci.* 2005, 46(10):3637-44). Similarly, healthy retinal ganglion cells are not incorporated into the retina when injected into the vitreous cavity of the eye (see, e.g., U.S. 2011/0003003 to Goldberg et al., the disclosure of which is hereby incorporated by reference).

SUMMARY OF THE INVENTION

In certain aspects, the invention is directed to magnetic eye shields that comprise a magnet. When worn by a patient, the magnetic eye shields are configured to generate an intraocular magnetic field of sufficient magnitude and direction to move a magnetic therapeutic and/or diagnostic agent positioned inside the eye to a target tissue within the eye. In some embodiments, the magnetic eye shield is selected from eye patches, or eyeglasses and goggles, among other possibilities.

Other aspects of the invention pertain to kits which comprise such magnetic eye shields as well as one or more additional components, for example, one or more containers of a magnetic diagnostic and/or or therapeutic agent.

Further aspects of the invention pertain to methods of treatment, which comprise intraocularly introducing a magnetic therapeutic and/or diagnostic agent into an eye of a patient and fitting a magnetic eye shield to the head of the patient. The magnetic eye shield is configured to generate an intraocular magnetic field of sufficient magnitude and direction to move the magnetic therapeutic and/or diagnostic agent positioned inside the eye to a target tissue within the eye, and the magnetic therapeutic and/or diagnostic agent may be introduced to the patient before or after fitting the magnetic eye shield to the head of the patient.

These and various other aspects and embodiments and as well as advantages of the present invention will become immediately apparent to those of ordinary skill in the art upon review of the Detailed Description and any appended claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

In the present disclosure, external magnetic eye shields are provided which are adapted to preferentially position magnetic diagnostic and/or or therapeutic agents which are placed within the eye of a subject for a variety of purposes. Though there are many eye shields for novelty, corrective or protective purposes, no shield is known to be available that by design provides a specifically desired intraocular magnetic field.

As used herein, "subjects" (also referred to as "patients") are vertebrate subjects, more typically mammalian subjects, including human subjects, pets and livestock.

Most materials can be classified as diamagnetic, paramagnetic, ferromagnetic or ferrimagnetic. Diamagnetic materials have a weak, negative susceptibility to magnetic fields and are thus slightly repelled by a magnetic field. Most elements in the periodic table, including copper, silver, and gold, are diamagnetic. Paramagnetic materials have a small, positive susceptibility to magnetic fields and are thus slightly attracted by a magnetic field. Paramagnetic materials include magnesium, molybdenum, lithium, and tantalum.

Ferromagnetic and ferrimagnetic materials have a large, positive susceptibility to an external magnetic field and thus are strongly attracted by a magnetic field. Examples of ferromagnetic materials include iron, nickel, cobalt and some rare earth elements (e.g., gadolinium, dysprosium, etc.). Examples of ferrimagnetic materials include magnetite, maghemite and various ferrites including nickel ferrite, cobalt ferrite, manganese ferrite, nickel zinc ferrite and manganese zinc ferrite. Superparamagnetism is a form of magnetism, which appears in small ferromagnetic or ferrimagnetic nanoparticles (e.g., small particles ranging from 1-25 nm in diameter, more typically, 1-10 nm in diameter). Superparamagnetic materials are attracted by a magnetic field but relax their magnetic dipole when the field is removed, decreasing their ability to attract each other in the absence of an external magnetic field. For diagnostic and therapeutic use, this relaxation may provide certain advantages, in some embodiments.

In the present disclosure, magnetic diagnostic and/or or therapeutic agents are preferably ferromagnetic or ferrimagnetic in nature, and more preferably superparamagnetic in certain applications. Specific examples of therapeutic agents include magnetic cells, for examples magnetic stem cells or magnetic ocular cells such as magnetic corneal endothelial cells and magnetic retinal pigment epithelial cells or magnetic photoreceptor cells. Further specific examples of magnetic therapeutic agents include magnetic growth factors, small molecule drugs, biological therapeutics, antibodies or antibody fragments, or cytokines. Specific examples of diagnostic agents include diagnostic agents such as magnetic fluorescent dyes, magnetic antibodies or antibody fragments, or magnetic particles that could be paired with diagnostic imaging or sensing devices such as optical coherence tomography, ultrasound, and photographic filters. Various materials can be rendered ferromagnetic or ferrimagnetic by associating them with ferromagnetic or ferrimagnetic particles such as microparticles or nanoparticles. For instance, (a) the agents can be attached to the surface of the particles by covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (b) the agents can be applied as a coating (biostable or biodegradable) that at least partially surrounds the particles, or (c) the particles can be bound to or endocytosed by the agent (e.g., a cell) and in either or both cases incorporated into the inside of the agent.

The eye shields of the present disclosure may cover one eye or both eyes. Moreover, the eye shields may be transparent (i.e., having a transmission of visible light of at least 20%), opaque or a combination of both. For example, in certain embodiments, the eye shield may be in the form of an eye patch that covers one or both eyes. In certain embodiments, the eye shield of the present disclosure may be transparent, in which case the eye shield may or may not provide vision correction for one or both eyes (e.g., an eye shield in the form of safety glasses, eyeglasses, safety goggles, corrective goggles, monocles, etc.). In certain embodiments the eye shield is positioned at a distance from the eye ranging from 5 to 20 mm (e.g., for eyeglasses or other shield where the patient opens his/her eyes). In certain embodiments the eye shield may sit flush with the eyelid in a closed position. In certain embodiments the eye shield may be concave to the eye and rest against the orbital rim peripherally. In certain embodiments the eye shield may rest directly on the cornea.

In order to generate a magnetic field having a desired magnitude and direction, the magnetic eye shields of the present disclosure are provided with one or more suitable magnets which may be selected, for example, from temporary magnets, permanent magnets and electromagnets.

Examples of permanent and temporary magnets include magnets that comprise iron, magnets that comprise neodymium, magnets that comprise cobalt, and magnets that comprise boron. Specific examples include rare earth magnets such as magnets that comprise neodymium, iron and boron (e.g., neodymium-iron-boron magnets, which commonly contain an alloy of neodymium, iron and boron, commonly in the form of a $Nd_2Fe_{14}B$ tetragonal crystalline structure), magnets that comprise samarium and cobalt (e.g., samarium-cobalt magnets, which are commonly available in two "series", specifically Series 1:5, which contain one atom of rare earth samarium for every five atoms of cobalt, and Series 2:17, which contain two atoms of rare-earth samarium and 13-17 atoms of transition metals, with the transition metal content being rich in cobalt). Specific examples further include magnets that comprise iron (e.g., ferrite magnets, which commonly have iron(III) oxide as the principle component) and magnets that comprise iron, aluminum, nickel and cobalt (e.g., Alnico magnets, which typically contain 8-12% Al, 15-26% Ni, 5-24% Co, up to 6% Cu, up to 1% Ti, and the balance Fe).

Specific examples of magnets include neodymium magnets. Neodymium magnets have a simple nomenclature, with the various grades starting "N (industry simplification of Neodymium) and is followed by a two digit number. This number represents the maximum energy product in Mega-Gauss Oersteds (MGOe). Neodymium magnets are commercially available in grades ranging from grade N24 up to grade N52, with a potential maximum of grade N64. In certain beneficial embodiments, neodymium magnets are employed with strength grade ranging from grade N42 to grade N64, more beneficially, ranging from grade N52 to grade N64.

An electromagnet is a type of magnet in which a magnetic field is produced by the flow of electric current, with the strength of magnetic field generated being proportional to the amount of current. The magnetic field disappears when the current is turned off. Typically, electromagnets comprise a conductor (e.g., an insulated wire, a printed or etched conductive line, etc.) in the form of a coil. To increase the magnetic field, a coil with multiple turns may be employed. The magnetic field may be increased by positioning a ferromagnetic material (e.g., iron, etc.) inside the coil to produce a ferromagnetic-core electromagnet.

Where an electromagnet is employed in the eye shields of the present disclosure, a power source is also typically provided. The power source may include, for instance, a non-rechargeable battery or may include a rechargeable battery, which may be recharged, for instance, by connection to an external voltage source via a conductor (e.g., via a wire connection) or by wireless recharging (e.g., by inductive charging). The power source may also include components which control the current within the electromagnet (and thus the field strength of the electromagnet) and which control the duty cycle of the electromagnet, in other words that amount of time and frequency the electromagnet is "on" (and generating a magnetic field) and when it is "off" (and not generating a field). One advantage of the use of an electromagnet in this embodiment is the ability to titrate the field strength exerted by the magnetic eye shield invention by changing the input current to the electromagnet.

Figure 2A:
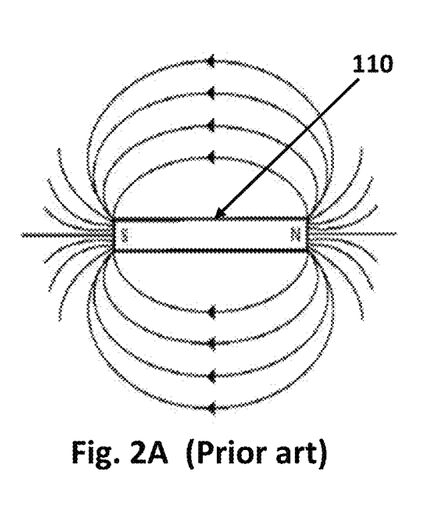
FIG. 2A is a schematic illustration of a bar magnet and associated field lines, in accordance with the prior art.
Figure 2B:
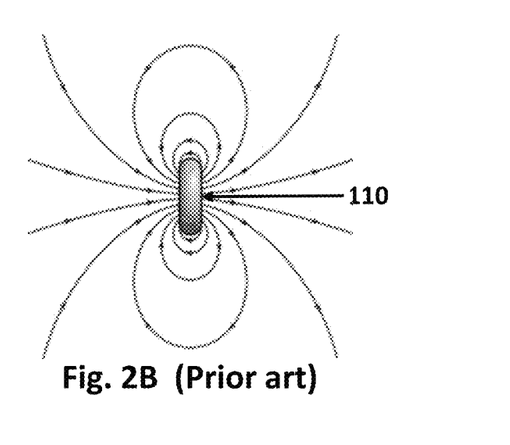
FIG. 2B is a schematic illustration of a ring-shaped magnet and associated field lines, in accordance with the prior art.

For purposes of illustration, two magnets and their associated magnetic field lines are shown schematically in FIGS. 2A and 2B.

FIG. 2A is a schematic illustration of a simple bar magnet 110 (e.g., a rare earth magnet, ferrite magnet, Alnico magnet, etc.) and the magnetic field lines associated with that magnet.

FIG. 2B is a schematic illustration of a ring-shaped magnet 110 and the magnetic field lines associated with the magnet. The ring-shaped magnet 110 may be for example, a temporary or permanent magnet (e.g., a rare earth, ferrite or Alnico magnet with poles on opposing faces of the ring) or the ring-shaped magnet 110 may be an electromagnet.

"Magnetic field lines" are lines that are drawn to show the direction of a magnetic field created by a magnet. These lines are also called "lines of force". Magnetic materials that are sufficiently mobile will migrate as a result of a magnetic field.

In various aspects, the present disclosure is directed to eye shields that generate an intraocular magnetic field that is sufficient to physically direct a magnetic therapeutic and/or diagnostic agent (e.g., a ferromagnetic material, ferrimagnetic material, etc.) positioned inside of the eye (e.g., placed in the eye by a patient or health care provider via surface application, infusion, injection, implantation, etc.) to one or more target tissues within the eye.

For instance, in one particular embodiment, the eye shield may generate a magnetic field having a magnitude and direction such that a magnetic diagnostic and/or therapeutic agent positioned in the anterior chamber of the eye is directed to the back surface of the cornea.

In another particular embodiment, the eye shield may generate a magnetic field having a magnitude and direction such that a magnetic diagnostic and/or therapeutic agent positioned in the vitreous cavity of the eye is directed towards the posterior pole of the eye.

Figure 3:
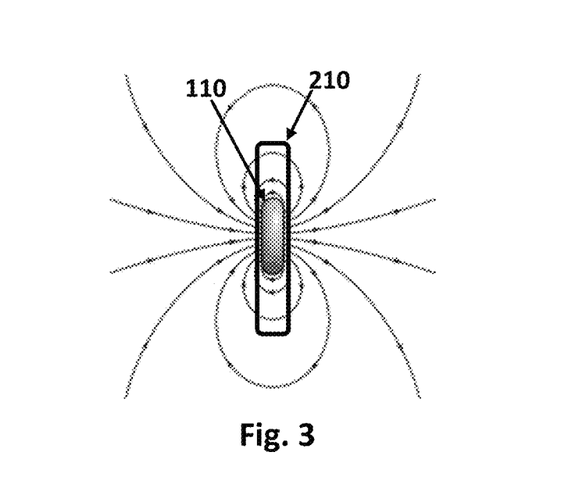
FIG. 3 is a schematic illustration of an eye shield with an associated ring-shaped magnet like that of FIG. 2B, in accordance with an embodiment of the present invention.

FIG. 3 is a schematic illustration of an eye shield 210 in accordance with the present disclosure within which is disposed a ring-shaped magnet 110 like that of FIG. 2B. The eye shield may be associated, for example, with an eye patch, eyeglasses, goggles or a variety of other devices. As seen schematically in FIG. 4, when an eye shield 210 with magnet 110 like that of FIG. 3 is placed adjacent to an eye 10, the magnetic field lines associated with such a device penetrate the eye, thereby exerting a force on any magnetic material that is disposed within the eye; that force may be attractive or repulsive.

Figure 4:
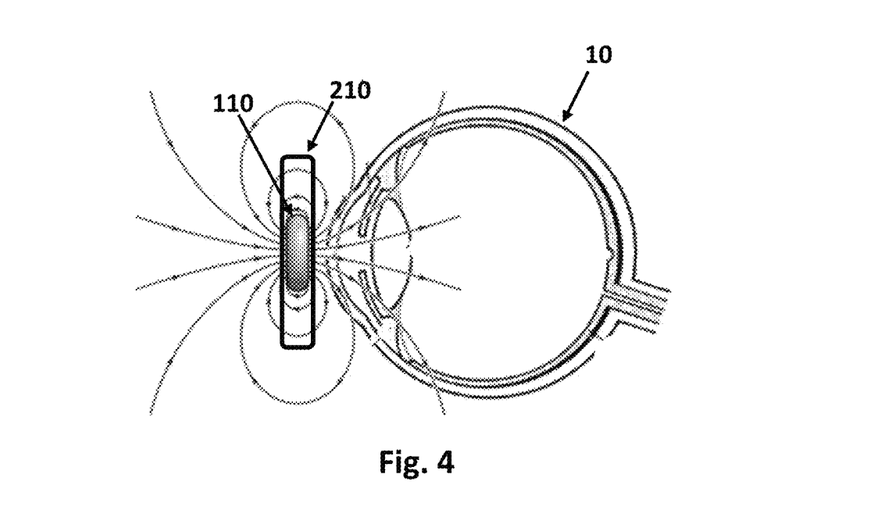
FIG. 4 is a schematic illustration showing an eye shield like that of FIG. 3 in close proximity to the eye, in accordance with an embodiment of the present invention.

While a ring-shaped magnet like that of FIG. 2B is shown in FIGS. 3 and 4, it should be clear from the present disclosure that the invention is not limited to such a magnet. Other types of magnets may be employed so long as a magnetic field is established within the eye that is capable of directing a magnetic therapeutic and/or diagnostic agent positioned within the eye to a targeted position within the eye.

Different magnetic fields can be used to attract or repel magnetic agents to different locations within the eye. In some embodiments, a magnet placed anterior to the eye will apply an attractive force to a magnetic material (e.g., a paramagnetic, ferromagnetic or ferrimagnetic material) within the eye in a direction that includes an anterior vector component. Consequently, magnets incorporated into external eye shields in accordance with the present disclosure may be used to draw intraocular magnetized material to the anterior aspect of the eye for diagnostic or therapeutic purposes. In other embodiments, a magnet placed anterior to the eye will apply a repulsive force to a magnetic material (e.g., a diamagnetic material) within the eye in a direction that includes a posterior vector component. Thus, a diamagnetic material may be used which is repulsed from the magnetic field, and, as in the above description, may drive the therapeutic and/or diagnostic agent to the posterior aspect of the eye.

The one or more magnets provided within the eye shields typically generate a magnetic field strength, measured at a distance from the magnet equal to the distance of the magnetic eye shield from the eye in that particular embodiment, ranging from 0.01 Tesla or less to 5 Tesla or more (e.g., ranging from 0.01 Tesla to 0.025 Tesla to 0.05 Tesla to 0.1 Tesla to 0.25 Tesla to 0.5 Tesla to 1.0 Tesla to 2.5 Tesla to 5.0 Tesla). More typical magnetic field strengths may range from 0.1 to 1.0 Tesla in order to allow a force sufficient to cover the 24 mm axial length of a typical human eye. The actual field strength will vary depending on various factors including the distance between the eye shield and the eye (e.g., the corneal apex), the depth of the target tissue within the eye, and the responsiveness or magnetic susceptibility of the therapeutic and/or diagnostic agent to the magnetic field, among other factors.

In some embodiments, the eye shields of the present disclosure are configured to provide a magnetic field of constant field strength in time. In other embodiments, the eye shields of the present disclosure are configured to provide a magnetic field of variable field strength as function of time. For example, it may be advantageous to be able to create a magnetic field that has an on/off duty cycle to control the extent and duration of the magnetic field, or to reverse the polarity. This may be able to help a magnetic agent placed inside the eye to circulate for extended periods of time within the eye. In another example, it may be advantageous to vibrate the magnetic agent inside the eye to generate mechanical forces or heat. In another example, it may be advantageous to titrate a magnetic field strength up or down to maximize the proposed delivery of the magnetic diagnostic and/or therapeutic device adjacent to or inside the eye.

Figure 5:
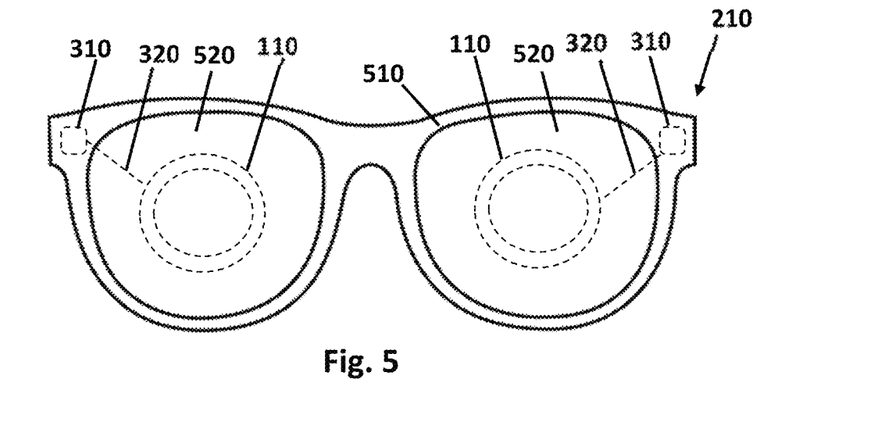
FIG. 5 is a schematic illustration of a pair of eyeglasses with an associated electromagnet, in accordance with an embodiment of the present invention.

Turning now to FIG. 5, a magnetic eye shield 210 in accordance with an embodiment of the present disclosure is schematically shown. The magnetic eye shield 210 shown includes a frame 510 with two lenses 520, which may be corrective or non-corrective. The magnetic eye shield 210 also includes two electromagnets 110 each of which comprises a conductive coil having one or more loops, which may be formed using lines of a transparent conductor (e.g., formed of indium tin oxide, fluorine doped tin oxide, doped zinc oxide, etc.) or using an opaque conductor (e.g., a metallic conductor such as copper, silver, gold, aluminum, etc.). In some embodiments, the center of each coil is centered on the optical axis of each eye. The magnetic eye shield 210 further includes two power supplies 310 which are connected to the electromagnets 110 via conductive lines 320 which, like the coils of the electromagnet 110, may be formed using a transparent conductor or an opaque conductor. The frame 510 may be secured to the head of the subject, for example, by traditional eyeglass temples (not shown).

Numerous variations are of course possible including one or more of the following among others: a single power supply may be used rather than a pair of supplies, the power supply/supplies may be located in the securement structure (e.g., temple) of the device, a temporary or permanent magnet may be used instead of an electromagnet (in which case there would be no need for the power supplies and conductive lines), the eyeglass frame may be replaced with a goggle frame, a strap may be used (rather than temples) as a securement structure, and the magnet may be located only on one side, i.e., the magnetic field may be applied to only one eye.

Figure 6:
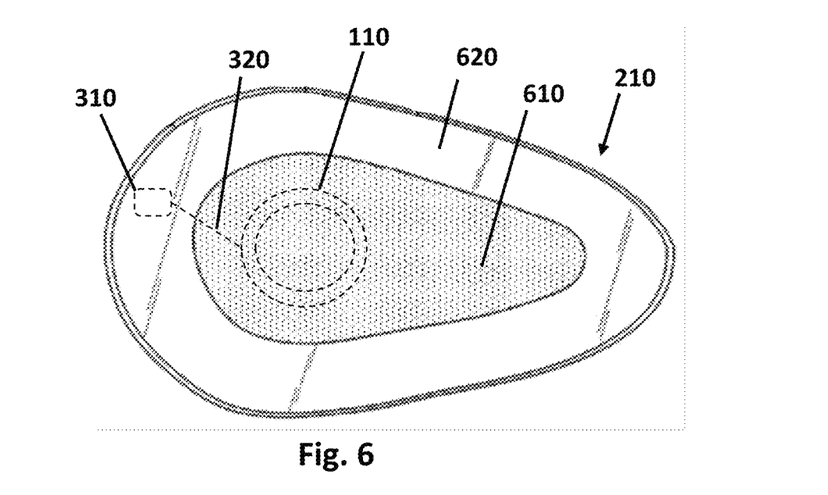
FIG. 6 is a schematic illustration of an eye patch with an associated electromagnet, in accordance with an embodiment of the present invention.

A magnetic eye shield 210 in accordance with another embodiment of the present disclosure is schematically shown in FIG. 6. The magnetic eye shield 210 shown includes an eye patch 610 which may include a securement structure such as an adhesive strip 620. The magnetic eye shield 210 also includes an electromagnet 110 which comprises a conductive coil having one or more loops, which may be formed using a suitable conductor, for instance, a transparent or opaque conductor such as those listed above, among others. In some embodiments, the center of each coil is centered on the optical axis of the eye. In some other embodiments, the center of the resultant magnetic field will be adjustable by being able to move (e.g., slide) the coil relative to the eye shield and thus permit treatment of the center of the optical axis for patients with strabismus (paralytic or restrictive) and thus an off-center optical axis. The magnetic eye shield 210 further includes a power supply 310 which is connected to the electromagnet 110 via conductive lines 320 formed of a suitable conductor.

As in FIG. 5, numerous variations are possible for the eye shield of FIG. 6 including one or more of the following among others: other methods of securement may be used including a strap, which may be elastic (the strap can extend around the head in order to secure it over the eye and be adjusted to ensure patient comfort), power supply/supplies may be located in the securement structure (e.g., strap) of the device, a temporary or permanent magnet may be used instead of an electromagnet (in which case there would be no need for the power supply and conductive lines), the shield may configured to sit flush with the eyelid or it may be concave to the eye and thus rest against the orbital rim peripherally.

One advantage of a patch (which contacts the eye or the eyelid) relative to glasses/goggles (which do not) is that a magnet with a lower power magnetic field may be employed to achieve a given intraocular field strength due to the differing distances from the eye.

As previously indicated, in certain preferred embodiments, eye shields of the present disclosure are provided with magnetic fields that are centered with the optical axis of the eye (see, e.g., the schematic illustration in FIG. 4) so as to direct magnetic therapeutic and/or diagnostic agents which have been positioned within the eye toward the optical axis of the eye. Because the magnet is disposed anterior to the eye, the magnetic field for such devices will be the strongest at the apex of the cornea. Consequently, magnetic therapeutic and/or diagnostic agents placed in the anterior chamber of the eye can be directed to the center of the cornea along the endothelial surface. In certain embodiments, this will help prevent the magnetic therapeutic and/or diagnostic agents from settling into the inferior anterior chamber where the cells may clog the trabecular meshwork and limit aqueous egress from the eye. Additionally, this will direct the material into the optical axis where a therapeutic and/or diagnostic effect is desired.

Figure 9:
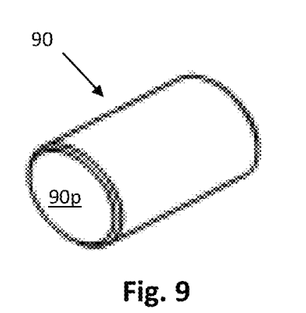
FIG. 9 is a schematic illustration of a cylindrical magnet for use in accordance with an embodiment of the present invention.

In certain embodiments a magnet having a cylindrical shape is positioned directly over the corneal apex. Such a magnet 90 is shown in FIG. 9A. Cylindrical magnets are beneficial in that the magnetic field of magnets of this type is typically strongest at the center of each of the opposing circular plates 90p (one plate associated with the north pole of the magnet and the other plate associated with the south pole of the magnet), with the magnetic field decreasing as one proceeds radially from the center of the plates 90p and as one proceeds normally from the surface of the plates 90p. Moreover, the smooth plates of cylindrical magnets add to patient comfort, as there are no sharp corners or edges on the magnet faces, which can rest directly on the patient's eyelid, if desired. In certain beneficial embodiments the magnet may be a neodymium magnet of grade 50N or more. In certain beneficial embodiments the magnet may have a diameter ranging from 6 mm to 20 mm in diameter, more typically ranging from 8 mm to 16 mm in diameter, and ranging from 5 mm to 40 mm in length, more typically ranging from 10 mm to 25 mm in length. Either the north pole of the magnet or the south pole of the magnet may face the patient's eye.

In other embodiments, magnetic eye shields may be configured to generate an intraocular magnetic field that is strongest in a position other than the corneal apex. For example, the magnetic eye shield may be configured to generate an intraocular magnetic field that is strongest at the periphery of the cornea, for example, at the iridocorneal angle (where the base of the iris attaches to the peripheral cornea and sclera), among other locations. These embodiments may be useful, for example, in treatment of glaucoma using trabecular meshwork cells, among other treatments.

Figure 7:
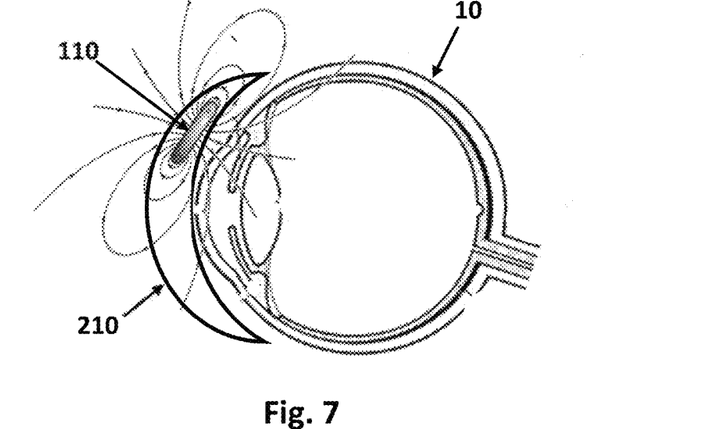
FIG. 7 is a schematic illustration of an eye patch with an associated ring-shaped magnet like that of FIG. 2B, in accordance with another embodiment of the present invention.

In some embodiments, a magnet having a magnetic field like that of FIG. 2B may be used to form a magnetic eye shield in which the magnet and its associated magnetic field are off-center with respect to the center of the eye shield. One example of an eye shield 210 with such an off-center magnet 110 is shown schematically in FIG. 7.

Figure 8:
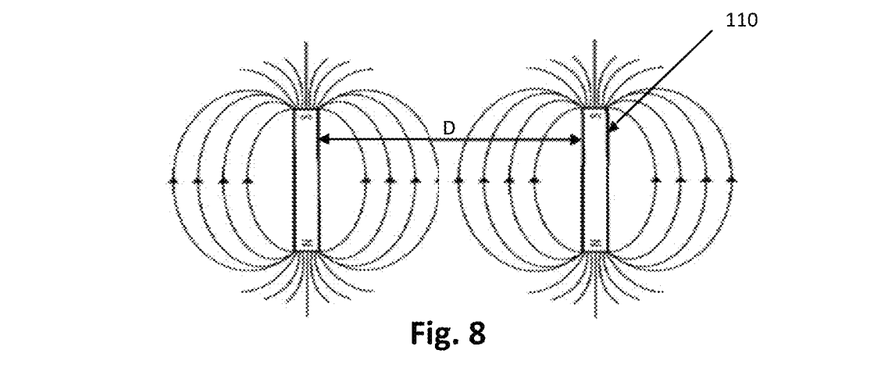
FIG. 8 is a schematic illustration of a cross-section of a bar magnet and associated field lines, for use in various embodiments of the invention.

In other embodiments, a magnet may be employed which is on-center with the regard to the eye shield and which nevertheless does not generate an intraocular magnetic field that is strongest at the corneal apex. For example, a ring-shaped magnet 110 like that shown in schematic cross-section in FIG. 8 (where D is the inside diameter of the magnet) may be employed, in which one surface represents a north pole of the magnet and another opposing surface represents a south pole of the magnet. Such a magnet is capable of providing a circular region of maximum intraocular field strength whose diameter can be adjusted based on the diameter of the magnet. For example, the diameter of the magnet may be adjusted to provide a maximum intraocular field strength at the periphery of the cornea, as indicated above. In this instance, the center of the magnet is preferably centered with respect to the eye shield. In other embodiments, the center of such a magnet may be off-center with regard to the eye shield.

Figure 10A:
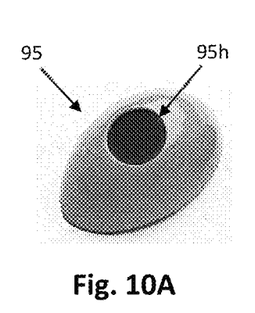
FIGS. 10A and 10B are schematic illustrations of eye cups for use as alignment components, in accordance with two embodiments of the present disclosure.
Figure 10B:
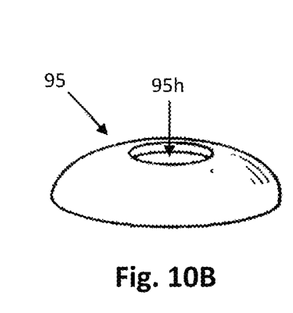

In some embodiments, eye shields in accordance with the present disclosure are provided with a magnetic shielding material, in order to reduce or eliminate interactions between the one or more magnets associated with the eye shield and objects (e.g., ferromagnetic or ferromagnetic objects) in the environment surrounding the patient including, for example, metal door frames and various loose metallic objects that may be nearby. Examples of magnetic shielding materials include various high-permeability shielding alloys such as nickel-iron alloys including permalloy (an alloy of nickel and iron) and mu-metal (an alloy of nickel, iron, copper and molybdenum or chromium), cobalt-based alloys, and ultra-low carbon steel, among others.

Where the eye shield is an eye patch, in order to enhance patient fit and comfort, it may be desirable to select a flexible or semi-rigid shielding material, for example, one or more sheets of flexible or semi-rigid material made of alloy that is used to reduce or eliminate an external magnetic field. Such materials are beneficially materials of high permeability and/or high saturation. Specific examples of such materials include MagnetShield™, which has a reported initial permeability of 200 and a saturation induction of 2.14 Tesla, and Giron™, which has a reported initial permeability of 500 and a saturation induction of 2 Tesla. Beneficially, the magnetic shielding material will be less than 3 mm in thickness, more beneficially less than 2 mm.

Where the eye shield is an eye patch, it may be desirable to provide the eye shield with an alignment component that is concave to the eye, thereby improving the ease at which the magnet is aligned relative to the eye (e.g., centered relative to the optical axis of the eye, positioned peripherally relative to the optical axis of the eye, etc.). For instance, in certain embodiments, the patch may incorporate as an alignment component an eye cup analogous to those used in tanning bed goggles (e.g., eye cup 95 in FIG. 10A) or a more spherical eye cup (e.g., eye cup 95 in FIG. 10B) which have a concave portion having dimensions that are somewhat complementary to the patient's eyeball and eyelid. Hole 95h may be aligned up with the optical axis of the patient's eye or offset relative to the optical axis of the eye. Hole 95h may be configured to receive and hold in place a magnet (e.g., a cylindrical magnet, among other possible shapes).

Further aspects of the present disclosure pertain to methods of treatment of a subject.

In a typical procedure, a magnetic therapeutic and/or diagnostic agent is introduced into the eye, for example, by injection, implantation, infusion, or surface application, among other techniques. Injection or implantation may be preferred in certain embodiments as more control is provided other than placement of the material within the eye which, in turn, assists in directing the agent to target tissue of choice. A magnetic eye shield such as one of those described elsewhere herein is also fitted to the head of the subject, either prior or subsequent to the introduction of the magnetic therapeutic and/or diagnostic agent. In various embodiments, care is taken to ensure that the magnetic field of the device is centered on the optical axis of the eye, as previously noted.

The eye shield is left in position for a time that is dependent upon various factors including the type of magnetic therapeutic and/or diagnostic agent employed and the length of time required to see a clinical effect, whether for therapeutic or diagnostic purposes. The time frame may varying anywhere from 10 minutes to indefinitely. Typical time frames may range, for example, from 3 hours to 72 hours, among others.

The eye shield may or may not be coated or covered or surrounded by a material that provides appropriate comfort or biocompatibility during its application. Such material could include but not be limited to any combination of polymers such as silicones, silicone hydrogels or other hydrogel materials (e.g., materials containing homopolymers or copolymers of two or more hydrogel monomers, such as 2-hydroxyethyl methacrylate, 1-vinyl-2-pyrrolidone, methacrylic acid, etc.), cotton materials, or other suitable materials.

In one particular embodiment, a procedure is provided in which a magnetic therapeutic and/or diagnostic agent is introduced into the anterior chamber, and a magnetic shield may be worn to draw those materials anteriorly to the apical aspect of the corneal endothelium. For example, magnetic corneal endothelial cells can be injected in to the anterior chamber of one or both eyes and a magnetic patch can be worn for anywhere from 10 minutes to indefinitely but typically for 1-3 days after injection to stimulate migration of the injected corneal endothelial cells to the back surface of the cornea to facilitate integration and retention of these cells into the host corneal endothelium.

Still further aspects of the present disclosure pertain to kits that are useful for diagnosing or treating a patient. The kits may include all or a subset of all the components useful for treating or diagnosing a patient in accordance with the present disclosure. The kits may include, for example, any combination of two or more of the following items: (a) a magnetic eye shield in accordance with the present disclosure (e.g., one or more eye patches, glasses, goggles, etc.), (b) a securement material such a strap or a suture material or an adhesive composition for affixing the eye shield to a patient's head, (c) one or more containers of a magnetic diagnostic and/or or therapeutic agent, for example, in a form that is suitable for immediate administration to a patient (e.g., in a liquid form suitable for injection, infusion or surface application, in a dry form suitable for implantation, etc.) or in a form suitable for administration upon addition of another component (e.g., in a dry form that is suitable for administration upon suspension or dissolution using a suitable liquid carrier, (d) one or more containers of a suitable liquid carrier (e.g. sterile water for injection, physiological saline, phosphate buffer, phosphate buffered saline, etc.) which may be used to reconstitute a magnetic diagnostic and/or or therapeutic agent in dry form or may be used to dilute a magnetic diagnostic and/or or therapeutic agent in liquid form, (e) an injection device (e.g., a combination syringe and needle or an iontophoresis device for administering a composition comprising a magnetic diagnostic and/or or therapeutic agent to the patients eye), (f) instructions for administering the magnetic compositions to a patient's eye and/or for fitting the magnetic eye shield to a patient's head, (g) packaging and information as required by a governmental regulatory agency that regulates cell therapy products, pharmaceuticals and/or medical devices, and (h) appropriate anesthetic and antiseptic supplies. In certain embodiments, the components of the kits are provided in a single sterile package for convenient use by a health care professional.

Where the kit comprises a magnet that is not an electromagnet (e.g., a rare earth magnet, ferrite magnet, Alnico magnet, etc.) in combination with a ferromagnetic or ferromagnetic diagnostic and/or therapeutic agent, it may be desirable to provide the kit with shielding to magnetically isolate the ferromagnetic or ferromagnetic agent from the magnet. For instance, if exposed to a magnetic field of sufficient magnitude for a sufficient time, the ferromagnetic or ferromagnetic diagnostic and/or therapeutic agent may itself become magnetized, which may lead, for example to clumping of the agent. In embodiments where shielding is desired, the ferromagnetic or ferromagnetic diagnostic and/or therapeutic agent, the magnet, or both may be enclosed within a suitable magnetic shielding material. Examples of magnetic shielding materials include various high-permeability shielding alloys such as nickel-iron alloys including permalloy (an alloy of nickel and iron) and mu-metal (an alloy of nickel, iron, copper and molybdenum or chromium), cobalt-based alloys, and ultra-low carbon steel, among others. Additional aspects of the invention are set forth in the following enumerated paragraphs:

Aspect 1. A magnetic eye shield comprising a magnet that when worn by a patient is configured to generate an intraocular magnetic field of sufficient magnitude and direction to move a magnetic therapeutic and/or diagnostic agent positioned inside the eye to a target tissue within the eye.

Aspect 2. The magnetic eye shield of aspect 1, wherein the magnetic eye shield is selected from an eye patches, eyeglasses and goggles.

Aspect 3. The magnetic eye shield of any of aspects 1-2, wherein the magnetic field generated by the magnet ranges from 0.1 Tesla to 10.0 Tesla.

Aspect 4. The magnetic eye shield of any of aspects 1-3, wherein the magnet is a rare earth magnet.

Aspect 5. The magnetic eye shield of any of aspects 1-3, wherein the magnet is an electromagnet comprising a conductive coil and a source of electrical power in electrical communication with the conductive coil.

Aspect 6. The magnetic eye shield of any of aspects 1-5, wherein the magnetic eye shield is configured to center the magnetic field of the magnet with the optical axis of the eye.

Aspect 7. The magnetic eye shield of any of aspects 1-5, wherein the magnetic eye shield is configured to generate an intraocular magnetic field that is strongest at the periphery of the cornea.

Aspect 8. The magnetic eye shield of any of aspects 1-5, wherein the magnetic eye shield is configured to generate an intraocular magnetic field that is strongest at the apex of the cornea.

Aspect 9. The magnetic eye shield of any of aspects 1-8, wherein the magnetic eye shield comprises a plurality of magnets.

Aspect 11. The magnetic eye shield of any of aspects 1-8, wherein the magnetic eye shield comprises a securement structure that is adapted to secure the magnetic eye shield to the head of the patient.

Aspect 12. The magnetic eye shield of aspect 10, wherein the securement structure is selected from a strap and adhesive strip.

Aspect 13. The magnetic eye shield of any of aspects 1-11, wherein the magnetic therapeutic and/or diagnostic agent is a ferromagnetic or ferrimagnetic therapeutic and/or diagnostic agent.

Aspect 14. The magnetic eye shield of any of aspects 1-13, wherein the magnetic eye shield further comprises one or more sheets of magnetic shielding material.

Aspect 15. The magnetic eye shield of any of aspects 1-13, wherein the magnetic eye shield further comprises two or more sheets of magnetic shielding material.

Aspect 16. The magnetic eye shield of any of aspects 14-15, wherein the magnetic shielding material is less than 3 mm in thickness.

Aspect 17. The magnetic eye shield of any of aspects 1-16, wherein the magnetic eye shield further comprises an alignment component aligning a patient's eye with respect to the magnetic field.

Aspect 18. The magnetic eye shield of any of aspects 1-16, wherein the magnetic eye shield further comprises an eye cup configured to align a patient's eye with respect to the magnetic field.

Aspect 19. A kit comprising a magnetic eye shield in accordance with any of aspects 1-18 and a container of a magnetic diagnostic and/or or therapeutic agent.

Aspect 20. The kit of aspect 19, further comprising an injection device.

Aspect 21. The kit of any of aspects 19-20, wherein the magnetic therapeutic and/or diagnostic agent is a ferromagnetic or ferrimagnetic therapeutic and/or diagnostic agent.

Aspect 22. The kit of any of aspects 19-20, wherein the magnetic therapeutic and/or diagnostic agent is selected from one or more of magnetic stem cells, magnetic corneal endothelial cells, magnetic retinal pigment epithelial cells, magnetic trabecular meshwork cells, magnetic antibodies, magnetic growth factors, and magnetic cytokines.

Aspect 23. The kit of any of aspects 19-22, wherein the magnet is an electromagnet comprising a conductive coil and wherein the kit further comprises an inductive charging unit.

Aspect 24. A method of treatment comprising intraocularly introducing a magnetic therapeutic and/or diagnostic agent into an eye of a patient and fitting a magnetic eye shield to the head of the patient, wherein the magnetic eye shield is configured to generate an intraocular magnetic field of sufficient magnitude and direction to move the magnetic therapeutic and/or diagnostic agent positioned inside the eye to a target tissue within the eye and wherein the magnetic therapeutic and/or diagnostic agent may be introduced to the patient before or after fitting the magnetic eye shield to the head of the patient.

Aspect 25. The method of aspect 24, wherein the magnetic therapeutic and/or diagnostic agent is injected into the anterior chamber of the eye and wherein the magnetic therapeutic and/or diagnostic agent is directed to the apex of the cornea.

Aspect 26. The method of aspect 24, wherein the magnetic therapeutic and/or diagnostic agent is injected into the anterior chamber of the eye and wherein the magnetic therapeutic and/or diagnostic agent is directed to the periphery of the cornea.

Aspect 27. The method of any of aspects 24-26, wherein the magnetic therapeutic and/or diagnostic agent is selected from one or more of magnetic stem cells, magnetic corneal endothelial cells, magnetic retinal pigment epithelial cells, magnetic trabecular meshwork cells, magnetic antibodies, magnetic growth factors, and magnetic cytokines.

Aspect 28. The method of any of aspects 24-27, wherein the magnetic therapeutic and/or diagnostic agent is selected from magnetic drugs and biological therapeutics.

EXAMPLE

Construction of an eye patch in accordance with an embodiment of the present disclosure will now be described. The eye patch comprises several components which will now be described.

The magnet in this Example is a neodymium magnet having a diameter of about 10 to 15 mm and a length of about 10 to 25 mm, for instance, a zinc coated N52 neodymium magnet having a diameter of 12.75 mm and a length of 20 mm, available, for example, from K&J Magnetics, Inc., Pipersville, Pa., USA.

Figure 11:
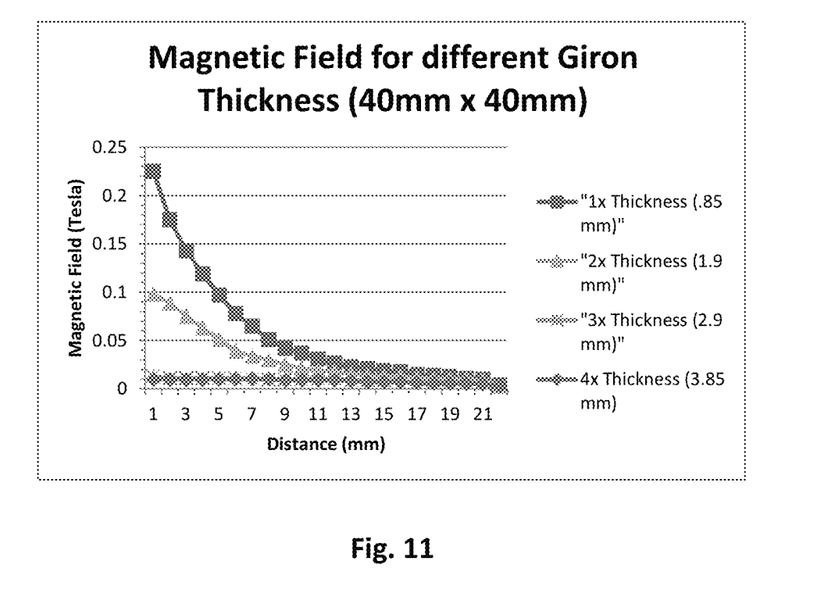
FIG. 11 is a graph of measured magnetic field emanating from a magnet that is shielded by 1, 2 and 4 sheets of shielding material, as a function of distance from the shielding material, in accordance with an embodiment of the present disclosure.
Figure 12:
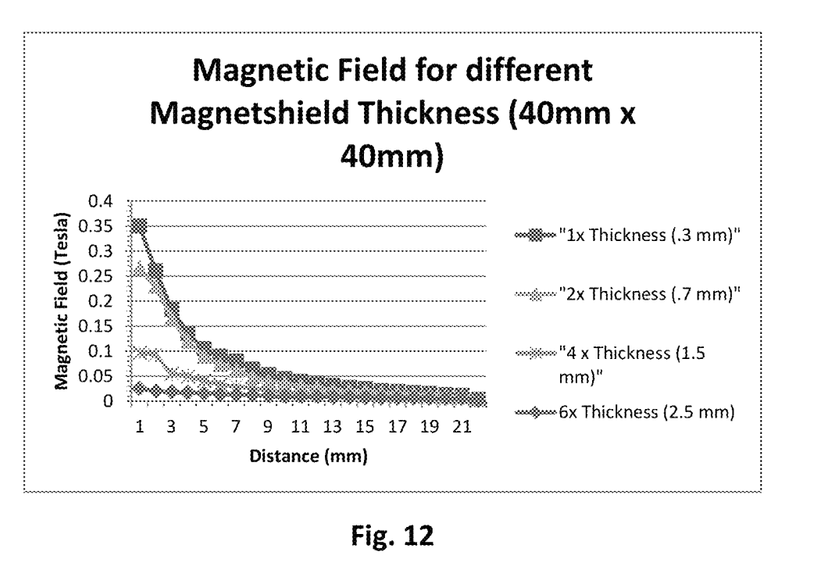
FIG. 12 is a graph of measured magnetic field emanating from a magnet that is shielded by 1, 2, 4 and 6 sheets of shielding material, as a function of distance from the shielding material, in accordance with an embodiment of the present disclosure.

The magnetic shielding component in this Example is a flexible magnetic component. Examples of flexible magnetic shielding materials include GIRON Magnetic Shielding Film, available in a thickness of 0.85 mm from Less EMF Inc., Latham, N.Y., USA and MagnetShield shielding film, available in a thickness of 0.3 mm from Electro Smog Shielding, Smethwick, UK. The ability of one or more sheets of the GIRON and MagnetShield films to shield against the N52 neodymium magnet was tested and the results are shown in FIG. 11 and FIG. 12. As can be seen from these figures, good shielding was achieved with three 40 mm×40 mm sheets of GIRON film (2.9 mm total thickness) and with six 40 mm×40 mm sheets of MagnetShield film (2.5 mm total thickness). A thinner material than GIRON, MagnetShield is more flexible than GIRON and can thus be shaped more readily than GIRON. Flexibility is a desired trait, because it allows the shield to better conform to each patient's unique face. Sheets of GIRON or MagnetShield may be cut to size, for example, using tin shears or by forming shapes in a stamping process, among other processes. If desired, sheets can be hole-punched or drilled to allow attachment of a strap. If desired, the sheets of shielding material may be attached to one another, for example, by applying a suitable adhesive, such as a metal epoxy adhesive, between the sheets. In certain embodiments, the adhesive is applied only at the center of the sheets, leaving the edges free to allow the sheets to slide relative to one another during flexing. In certain embodiments, the magnet brings the sheets of shielding material together, making attachment unnecessary. In certain embodiments, the edges of the stacked sheets may be covered by, for example, by a cloth (e.g., a cloth garter), a foam, or a flexible frame (e.g., an injection molded frame) with a slotted perimeter into which the sheets can be inserted and held (e.g., analogous to the flexible frames that are used to hold and surround a ski goggle lens, for one or both eyes). It may also be desirable to attach the magnet to the outer surface of the flexible shield, for example, using a suitable adhesive such as an epoxy adhesive, to ensure that there is no movement of the magnet relative to the shield, for example, by the patient or by movement relative to the shield if the magnet is accidentally dropped or pushed.

In some embodiments, an optional elastic headband may used as a strap around the head, holding the eye patch in place and better conforming the magnetic shielding material to the patient's face. This feature allows for minimal movement of the eye patch and yet can still be easily removed, for example, to add eye drops. This material should be elastic to allow for the eye patch to be pulled toward the face. Sports headband materials may be used for this application because they are made to not be exceptionally tight and still add the security desired for the device. The strap may be made adjustable in length in case the patch is either too tight or not held tightly enough against the patients face. A specific example of a strap material is a silicone backed elastic such as that available from Sew Sassy Fabrics, Huntsville, Ala., USA. A tension adjusting part like those commonly used among sunglass wearers, for example, a cord lock (e.g., a toggle spring stop single hole string cord lock, etc.), may be used to adjust strap tension.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A magnetic eye shield comprising a single magnet that when worn by a patient is configured to generate an intraocular magnetic field of sufficient magnitude and direction to move a magnetic therapeutic and/or diagnostic agent positioned inside the eye to a target tissue within the eye, (a) wherein the magnetic eye shield is configured to generate an intraocular magnetic field that is strongest at the periphery of the cornea or (b) wherein the magnetic eye shield is configured to generate an intraocular magnetic field that is strongest at the apex of the cornea.

2. The magnetic eye shield of claim 1, wherein the magnetic eye shield is selected from an eye patches, eyeglasses and goggles.

3. The magnetic eye shield of claim 1, wherein the magnetic field generated by the magnet ranges from 0.1 Tesla to 10.0 Tesla.

4. The magnetic eye shield of claim 1, wherein the magnet is a rare earth magnet.

5. The magnetic eye shield of claim 1, wherein the magnet is an electromagnet comprising a conductive coil and a source of electrical power in electrical communication with the conductive coil.

6. The magnetic eye shield of claim 1, wherein the magnetic eye shield is configured to center the magnetic field of the magnet with the optical axis of the eye.

7. The magnetic eye shield of claim 1, wherein the magnetic eye shield is configured to generate an intraocular magnetic field that is strongest at the periphery of the cornea.

8. The magnetic eye shield of claim 1, wherein the magnetic eye shield is configured to generate an intraocular magnetic field that is strongest at the apex of the cornea.

9. The magnetic eye shield of claim 1, wherein the magnetic eye shield comprises a securement structure that is adapted to secure the magnetic eye shield to the head of the patient.

10. The magnetic eye shield of claim 9, wherein the securement structure is selected from a strap and adhesive strip.

11. The magnetic eye shield of claim 1, wherein the magnetic therapeutic and/or diagnostic agent is a ferromagnetic or ferrimagnetic therapeutic and/or diagnostic agent.

12. A kit comprising a magnetic eye shield in accordance with claim 1 and a container of a magnetic diagnostic and/or or therapeutic agent.

13. The kit of claim 12, further comprising an injection device.

14. The kit of claim 12, wherein the magnetic therapeutic and/or diagnostic agent is a ferromagnetic or ferrimagnetic therapeutic and/or diagnostic agent.

15. The kit of claim 12, wherein the magnetic therapeutic and/or diagnostic agent is selected from one or more of magnetic stem cells, magnetic corneal endothelial cells, magnetic retinal pigment epithelial cells, magnetic trabecular meshwork cells, magnetic antibodies, magnetic growth factors, and magnetic cytokines.

16. The kit of claim 12, wherein the magnet is an electromagnet comprising a conductive coil and wherein the kit further comprises an inductive charging unit.

17. The kit of claim 12, wherein the container of magnetic diagnostic and/or or therapeutic agent is enclosed within a magnetic shielding material.

18. The magnetic eye shield of claim 1, wherein the sing magnet has a cylindrical shape or a ring shape.

19. A method of treatment comprising intraocularly introducing a magnetic therapeutic and/or diagnostic agent into an eye of a patient and fitting a magnetic eye shield to the head of the patient, wherein the magnetic eye shield comprises a single magnet and is configured to generate an intraocular magnetic field of sufficient magnitude and direction to move the magnetic therapeutic and/or diagnostic agent positioned inside the eye to a target tissue within the eye and wherein the magnetic therapeutic and/or diagnostic agent may be introduced to the patient before or after fitting the magnetic eye shield to the head of the patient, wherein the magnetic therapeutic and/or diagnostic agent is injected into the anterior chamber of the eye and (a) wherein the magnetic therapeutic and/or diagnostic agent is directed to the apex of the cornea or (b) wherein the magnetic therapeutic and/or diagnostic agent is directed to the periphery of the cornea.

20. The method of claim 19, wherein the magnetic therapeutic and/or diagnostic agent is injected into the anterior chamber of the eye and wherein the magnetic therapeutic and/or diagnostic agent is directed to the apex of the cornea.

21. The method of claim 19, wherein the magnetic therapeutic and/or diagnostic agent is injected into the anterior chamber of the eye and wherein the magnetic therapeutic and/or diagnostic agent is directed to the periphery of the cornea.

22. The method of claim 19, wherein the magnetic therapeutic and/or diagnostic agent is selected from one or more of magnetic stem cells, magnetic corneal endothelial cells, magnetic retinal pigment epithelial cells, magnetic trabecular meshwork cells, magnetic antibodies, magnetic growth factors, and magnetic cytokines.

23. The method of claim 19, wherein the magnetic therapeutic and/or diagnostic agent is selected from magnetic drugs and biological therapeutics.

24. A magnetic eye shield comprising a magnet that when worn by a patient is configured to generate an intraocular magnetic field of sufficient magnitude and direction to move a magnetic therapeutic and/or diagnostic agent positioned inside the eye to a target tissue within the eye, wherein the magnetic eye shield further comprises one or more sheets of magnetic shielding material and wherein the magnetic field generated by the magnet ranges from 0.1 Tesla to 10.0 Tesla, wherein the magnetic shielding material is configured to magnetically shield objects surrounding the patent from the 0.1 Tesla to 10.0 Tesla magnetic field generated by the magnet.

25. The magnetic eye shield of claim 24, wherein the magnetic shielding material is less than 3 mm in thickness and wherein the magnetic field generated by the magnet ranges from 1 Tesla to 2.5 Tesla.

26. The magnetic eye shield of claim 24, wherein the eye shield is an eye patch and wherein the magnetic eye shield is a flexible eye shield, thereby enhancing patient fit and comfort.

27. The magnetic eye shield of claim 24, wherein a material for the magnetic eye shield is selected from nickel-iron alloys, cobalt-based alloys, and ultra-low carbon steel.

28. The magnetic eye shield of claim 24, wherein the magnet is a single magnet and has a cylindrical shape or a ring shape.

* * * * *